United States Patent
Urban et al.

(10) Patent No.: US 9,480,639 B2
(45) Date of Patent: Nov. 1, 2016

(54) METHOD FOR EXTRACTING PHENOLIC COMPOUNDS FROM OLIVE FRUIT WATER AND PREPARATION OF AN EXTRACT TITRATED WITH OLIVE AND GRAPE POLYPHENOLS

(75) Inventors: Nelly Urban, Sainte Anastasie (FR); Manuel Dornier, Clapiers (FR); Dominique Pallet, Montpellier (FR); Max Reynes, Clapiers (FR)

(73) Assignees: Centre de Cooperation Internationale en Recherche Agronomique Pour le Developpement (CIRAD), Paris (FR); GRAP'SUD, Cruviers-Lascours (FR); Centre International d'Etudes Superieures en Sciences Agronomiques (Montpellier Sup Agro), Montpellier (FR)

( * ) Notice: Subject to any disclaimer, the term of this patent is extended or adjusted under 35 U.S.C. 154(b) by 879 days.

(21) Appl. No.: 13/148,429

(22) PCT Filed: Feb. 18, 2010

(86) PCT No.: PCT/FR2010/000137
§ 371 (c)(1),
(2), (4) Date: Nov. 11, 2011

(87) PCT Pub. No.: WO2010/094860
PCT Pub. Date: Aug. 26, 2010

(65) Prior Publication Data
US 2012/0045406 A1   Feb. 23, 2012

(30) Foreign Application Priority Data
Feb. 18, 2009   (FR) ..................................... 09 00752

(51) Int. Cl.
| | | |
|---|---|---|
| *A61K 8/34* | (2006.01) |
| *C07C 37/82* | (2006.01) |
| *A23L 1/30* | (2006.01) |
| *C09K 15/08* | (2006.01) |
| *A23L 1/28* | (2006.01) |
| *A61Q 19/02* | (2006.01) |
| *A61Q 19/00* | (2006.01) |
| *A61K 8/97* | (2006.01) |
| *A61Q 19/08* | (2006.01) |
| *C07C 37/00* | (2006.01) |
| *C07C 37/68* | (2006.01) |

(52) U.S. Cl.
CPC ................ *A61K 8/97* (2013.01); *A23L 1/3002* (2013.01); *A61Q 19/02* (2013.01); *A61Q 19/08* (2013.01); *C07C 37/004* (2013.01); *C07C 37/685* (2013.01); *A61K 2800/522* (2013.01)

(58) Field of Classification Search
None
See application file for complete search history.

(56) References Cited

U.S. PATENT DOCUMENTS

| | | | |
|---|---|---|---|
| 6,361,803 B1 | 3/2002 | Cuomo et al. |
| 6,416,808 B1 | 7/2002 | Crea |
| 2007/0077279 A1 | 4/2007 | Schweikert et al. |
| 2007/0134400 A1* | 6/2007 | Kealey et al. ................ 426/631 |

FOREIGN PATENT DOCUMENTS

| | | |
|---|---|---|
| EP | 1 623 960 A1 | 2/2006 |
| EP | 1 844 666 A1 | 10/2007 |
| ES | 2 177 457 A1 | 12/2002 |
| FR | 2 772 235 A1 | 6/1999 |
| WO | WO 2005/123603 A1 | 12/2005 |
| WO | WO 2006/005986 A1 | 1/2006 |
| WO | WO 2007/013032 A2 | 2/2007 |

OTHER PUBLICATIONS

International Search Report Application No. PCT/FR29010/000137 dated Mar. 11, 2011.
Written Opinion for International Application No. PCT/FR29010/000137 (undated).
Skaltsounis, L. et al., *MINOS Project Process Development for an Integrated Olive Mill Waste Management Recovering Natural Antioxidants and Producing Organic Fertilizer*, Terra Nova Ltd., Manual, Apr. 2004, 13 pages.

* cited by examiner

*Primary Examiner* — Patricia Duffy
*Assistant Examiner* — Garen Gotfredson
(74) *Attorney, Agent, or Firm* — Alston & Bird LLP

(57) ABSTRACT

The present invention relates to a method for extracting phenolic compounds with low molecular weights from olive fruit water; the invention also relates to compositions enriched with phenolic compounds including at least 40% of dry matter, said dry matter consisting of at least 30% hydroxytyrosol; the invention also relates to a method for drying said compositions by spraying using grape polyphenol extracts as a drying medium as well as to powders titrated with phenolic compounds of olives and grapes obtained after drying.

5 Claims, No Drawings

METHOD FOR EXTRACTING PHENOLIC COMPOUNDS FROM OLIVE FRUIT WATER AND PREPARATION OF AN EXTRACT TITRATED WITH OLIVE AND GRAPE POLYPHENOLS

FIELD OF THE INVENTION

The present invention relates to a method for extracting low-molecular-weight phenolic compounds from olive wastewaters; it also relates to compositions enriched with phenolic compounds comprising at least 40% of dry matter, said dry matter being composed of at least 30% of hydroxytyrosol; the invention also relates to a method for drying said compositions by spraying using grape polyphenol extracts as a drying support and also to the powders titrated with respect to olive and grape phenolic compounds, which are obtained after drying.

BACKGROUND OF THE INVENTION

The method for producing olive oil consists in crushing (milling) whole olives until a fine paste or pulp is obtained. During this step, the milled olive material can be constantly washed with water. The paste is then mechanically pressed (pressing) in order to extract therefrom its liquid content. The liquid obtained is then decanted in order to separate the two phases of which it is composed: the oil and the aqueous phase. The waters from washing the milled material and the aqueous phase that are recovered at the end of the pressing are called wastewaters or alternatively vegetable waters. These waters represent approximately 60% of the weight of the olive.

These wastewaters are very rich in antioxidant phenolic compounds; an antioxidant phenolic compound that is particularly desired is hydroxytyrosol; it is present at a content of 0.1 to 2 g/l in the vegetable waters.

Hydroxytyrosol is a simple phenolic compound which has a side chain of alcohol type at position 1 of the aromatic ring, and also two hydroxyl substitutions at positions 3 and 4 of said ring. This compound belongs to the family of ortho-diphenols, which are compounds generally known to have advantageous antioxidant properties.

Its consumption appears to contribute to the beneficial effect of the Cretan diet on human health. Numerous research studies carried out on hydroxytyrosol have shown the advantage of this compound as an antioxidant. The antioxidant activity of hydroxytyrosol confers thereon fatty-substance-preserving agent properties; it is also known for its antibacterial, antiviral and antifungal properties.

This compound is therefore considered to be a very good food supplement or additive and to be an active agent that is of use for reinforcing cell protection with respect to oxidative stress and to the pathological conditions that it generates.

Owing to the advantage, in particular for the food and cosmetics industries, that hydroxytyrosol, and more generally olive polyphenols, represent, various attempts at recovering the by-products rich in phenolic compounds, such as wastewaters (Visioli et al. "*Waste waters from olive oil production are rich in natural antioxidants*" Experientia, 1995; 51: 32-34), have been carried out.

U.S. Pat. No. 6,361,803 thus describes a method for extracting antioxidant compositions from olive-derived products: pulp, oil or alternatively wastewaters from olives at various stages of maturity. When the starting product consists of wastewaters, the method consists in treating them on an adsorbent polymeric resin which traps the antioxidant compounds, and then in washing the resin with an organic polar solvent in order to recover the antioxidant compounds.

However, the implementation of this method appears to be less suitable for the wastewaters than for the other olive-derived products. Specifically, comparison of the phenolic-compound composition of extracts obtained from various starting materials shows that the extract obtained from wastewaters has a low phenolic-compound content: 16.8%; in addition, the antioxidant activity of this extract is the lowest of all the extracts obtained.

European patent application EP 1 623 960 describes a method for preparing tyrosol and/or hydroxytyrosol from olive wastewaters (vegetable waters) which comprises steps of:
  physical separation involving several membrane treatments (microfiltration, ultrafiltration, nanofiltration and reverse osmosis) of the vegetable waters, preferably at a neutral or alkaline pH;
  chromatographic separation of the tyrosol, of the hydroxytyrosol and of other phenolic compounds from the concentrate obtained after the final membrane treatment;
  catalytic conversion of the tyrosol to hydroxytyrosol in the presence of a mixture of methylrhenium trioxide (MTO) and of hydrogen peroxide;
  recovery of the aqueous phase comprising the antioxidant phenolic compounds.

This method has the drawback of implementing a chemical hydroxylation of the tyrosol to give hydroxytyrosol; however, in view of the subsequent consumption of the hydroxytyrosol obtained, it is necessary to eliminate the catalysts, in particular the methylrhenium trioxide, which is a strong irritant. In addition, this method comprises a very large number of steps: example 1 of this document implements a method which comprises no less than 13 membrane treatments. It is therefore very long to implement and expensive in terms of technical and human means, and its proportioning to the industrial scale is not economically envisionable.

The same is true for the method described in international application WO 2005/123603, which is intended for the fractionation of olive wastewaters with the aim of recovering them. This method comprises a step of adjustment of the pH; of enzymatic hydrolysis of the cellulose, hemicellulose and pectin contained in the wastewaters; of centrifugation; of tangential microfiltration; of tangential ultrafiltration; of diafiltration; of tangential nanofiltration and of reverse osmosis.

International application WO 2007/013032 describes a method for obtaining hydroxytyrosol-rich concentrates in particular from wastewaters; this method combines at least two steps:
  an extraction of hydroxytyrosol and of other bioactive compounds by means of a supercritical fluid and/or by nanofiltration; and
  a reverse osmosis.

The extraction by means of a supercritical fluid requires the use of very high pressures (above 74 bar when $CO_2$ is used as supercritical fluid), and it is therefore a method that is complex and also expensive to implement. In addition, reverse osmosis is a process which results in the concentrating of an extract through removal of water; in particular, reverse osmosis does not allow a selective enrichment with low-molecular-weight phenolic compounds.

U.S. Pat. No. 6,416,808 describes a method for obtaining a hydroxytyrosol-rich composition from olive wastewaters, comprising the following steps: (i) production of a wastewater from depitted olives; (ii) addition of a sufficient amount of acid, preferably of citric acid, to reach a pH of between 1 and 5; (iii) incubation of the acidified wastewaters for at least two months in order for the oleuropein to be hydrolyzed to hydroxytyrosol. The method can also comprise a step of extraction of the hydroxytyrosol with an organic solvent, a high performance liquid chromatography (HPLC) or alternatively an extraction with supercritical fluid.

Although it produces hydroxytyrosol-enriched compositions, this method, when it implements an extraction by HPLC or with supercritical fluid, is too expensive to be used on the industrial scale. In addition, the liquid-liquid extraction uses toxic organic solvents which are not compatible with use of the extract obtained in the cosmetics or food industries.

Thus, the methods described in the prior art do not give complete satisfaction and there remains the need to develop a method for extracting low-molecular-weight phenolic compounds from olive wastewaters which is simple and suitable for industrial implementation.

SUMMARY OF THE INVENTION

The applicant set itself the objective of proposing a method which results in a fractionation of the phenols contained in the vegetable waters in order to separate the low-molecular-weight phenolic fraction from the compounds of higher molecular weight, such as oleuropein and verbascoside.

In order to provide an advantage in the context of the present invention, it is necessary for the method to enable a selective enrichment with hydroxytyrosol and with tyrosol. This is what the applicant has achieved by selecting nanofiltration membranes which exhibit the lowest possible retention of hydroxytyrosol and of tyrosol, and, simultaneously, a maximum retention of the other phenolic compounds, in particular of the polyphenolic compounds. Thus, the use of the nanofiltration membranes selected makes it possible to increase by 1.5 to 3.5-fold the phenolic-compound content by weight of the dry matter of the permeates, and in particular by 2 to 20-fold the hydroxytyrosol content by weight of the dry matter of the permeates resulting from the nanofiltration treatment; the permeates are therefore significantly enriched with low-molecular-weight phenolic compounds.

The dry matter of a sample is measured by drying the sample; the percentage of dry matter is then determined by the ratio between the weight of the dry matter and the total weight of the sample.

Unless otherwise specified, in what follows, the concentrations are expressed as percentages by weight.

The term "retentate" is intended to mean the fraction of a sample that is retained by a membrane during the membrane separation treatment of said sample.

The term "permeate" is intended to mean the fraction of a sample which passes through a membrane during the membrane separation treatment of said sample.

The term "membrane separation treatment" is intended to mean, in the context of the present invention, a method of filtration—microfiltration, ultrafiltration, nanofiltration—or of reverse osmosis.

The term "eluate" is intended to mean the product obtained by redissolving, with a solvent, one or more substances adsorbed onto a support; the eluate therefore comprises the solvent and said substance(s).

The term "wastewaters" or "vegetable waters" is intended to mean the waters generated during the production of olive oil. The dry matter content of the vegetable waters is variable and depends on the process used in the oil mill; by way of indication, unclarified crude vegetable waters can contain between 3 and 15% of dry matter.

DETAILED DESCRIPTION OF THE INVENTION

According to a first of its subjects, the present invention relates to a method for extracting low-molecular-weight phenolic compounds from olive wastewaters, comprising:
  (a) a step of clarification of said wastewaters;
  (b) a step of tangential ultrafiltration of the clarified wastewaters obtained in step (a) through a tubular ceramic membrane having a cutoff threshold of between 100 and 200 kDa and of recovery of the permeate;

said method being characterized in that it also comprises:
  (c) a step of nanofiltration of said permeate obtained in step (b) through a spiral organic membrane having a cutoff threshold of between 150 and 400 Da at a pressure of between 1 and 3 MPa; said membrane is such that it comprises an active layer comprising at least 50% of polyamide and that it makes it possible to obtain a retentate comprising at least 70%, preferably between 70 and 90%, and more preferentially at least 80%, of the dry matter contained in said wastewaters, and at most 25%, or at most 20%, of hydroxytyrosol, and
  (d) a step of adsorption of the phenolic compounds contained in the permeate obtained in step (c) by passing the latter over a polymeric matrix, followed by elution of the phenolic compounds adsorbed onto said matrix, with an organic polar solvent, and obtaining of an eluate.

The method according to the invention has the advantage of resulting, with only two steps of membrane treatment (ultrafiltration and nanofiltration), in a selective enrichment with low-molecular-weight phenolic compounds. This method also has the originality of making it possible to separate phenolic compounds of the wastewaters into various fractions: whereas the known methods concentrate all the phenolic compounds of the wastewaters by means of membrane treatments (the phenolic compounds are then recovered in the retentate), in the method according to the invention, the nanofiltration membranes used allow separation of the phenolic compounds, the phenolic compounds of interest then being recovered in the permeate.

In order to be used in the method according to the invention, the wastewaters can comprise up to 15% of dry matter. The percentage of dry matter of the wastewaters is the ratio between the weight of the dry matter and the total weight of the wastewaters. In particular, the wastewaters have a dry matter content of between 3 and 7%. The use of vegetable waters comprising more than 7% of dry matter requires a prior treatment such as a dilution.

The expression "low-molecular-weight phenolic compounds" is intended to mean compounds having a molecular weight of less than or equal to 400 Da. In particular, the low-molecular-weight phenolic compounds are hydroxytyrosol, tyrosol, phenolic acids such as hydroxycinnamic acids, for instance ferulic acid, coumaric acid or cafeic acid, or esters thereof, for instance chlorogenic acid.

The clarification consists of a solid-liquid extraction, such as filtration, centrifugation or else decanting, of the wastewaters.

The term "filtration" is intended to mean a method for separating the constituents of a mixture which has a liquid phase and a solid phase, through a porous medium. For implementing step (a) of the method of the invention, it is possible to use a clarifying filtration, i.e. a porous medium such that the pore diameter is between 10 and 450 µm; the filtration can be carried out by means of cartridge filters, candle filters, plate filters, sand filters, press filters or rotary filters under vacuum.

Centrifugation is a technique that uses centrifugal force to separate solid elements in suspension in a fluid; this technique is implemented by means of a centrifuge, the characteristics of which will be selected by those skilled in the art according to the vegetable waters to be treated; by way of example, mention may be made of tubular bowl centrifuges, concentric-chamber bowl centrifuges, plate centrifuges or centrifugal decanter centrifuges.

Finally, decanting is an operation of mechanical separation, under the action of gravity, of several immiscible phases, at least one of which is liquid. It is thus possible to separate insoluble solids in suspension in a liquid, as in the case of vegetable waters. For carrying out such decanting, it is possible to use a decanter (also called thickener), the characteristics of which will be adjusted by those skilled in the art according to the vegetable waters to be treated; mention may in particular be made of batch decanters and continuous decanters, optionally comprising partitions or stages.

Preferably, the clarification is carried out by means of a filtration operation.

The tangential ultrafiltration carried out in step (b) of the method according to the invention is a mechanical method of liquid-phase separation based on the molecular sieving properties of a porous membrane tangentially swept with a liquid containing the constituents to be separated. In the context of the present method, the tangential ultrafiltration is carried out with tubular ceramic membranes having a cutoff threshold preferably of 150 kDa, for instance the ultrafiltration membranes provided by the companies Tami and Exekia. The method is carried out at low pressure, i.e. less than or equal to 0.1 MPa.

After the clarified wastewaters obtained in step (a) have passed through the ultrafiltration membrane, two fractions are obtained: the permeate which contains the solvent and all the dissolved molecules which have a diameter smaller than the diameter of the pores of the membrane; and the retentate which is enriched, relative to the initial liquid, with molecules and compounds which have a diameter larger than the diameter of the pores of the membrane.

Step (c) consists of a nanofiltration treatment of the permeate obtained in step (b). Nanofiltration is a method of separation carried out by applying a pressure, which is the driving force thereof, on a semipermeable membrane; it is characterized by the nature of the membrane used, which defines the size of the particles targeted and the operating pressure.

In the context of the method according to the present invention, the nanofiltration step is carried out on a spiral organic membrane having a cutoff threshold of between 150 and 400 Da, preferably between 300 and 400 Da, the active layer of which comprises at least 50% of polyamide. Under these conditions, the nanofiltration of the permeate resulting from step (b) produces a second permeate resulting from step (c) containing the low-molecular-weight phenolic compounds (hydroxytyrosol, tyrosol and phenolic acids).

More specifically, it has been shown in example 1 hereinafter that only the spiral organic membranes having a cutoff threshold of between 150 and 400 Da, the active layer of which comprises at least 50% of polyamide, and which have the characteristics described hereinafter, result in satisfactory fractionation of the phenolic compounds of the vegetable waters: thus, the membranes of which the use produces a retentate comprising at least 70%, preferably between 70 and 90%, and more preferentially at least 80%, of the dry matter contained in said wastewaters, and at most 25%, or at most 20%, of hydroxytyrosol, are of use according to the invention. These values are, for example, obtained during the treatment of vegetable waters containing 4% of dry matter in the context of tests on a pilot laboratory apparatus having a nominal volume of 3 l, in the planar configuration, with a useful membrane surface area of $1.5 \times 10^{-2}$ $m^{-2}$, a transmembrane pressure of between 1 and 3 MPa and a tangential speed of 1 $m \cdot s^{-1}$.

In addition, the nanofiltration membranes that can be used in the method of the present invention are preferentially selected from those having a permeate flow density of at least 10 $l \cdot h^{-1} \cdot m^{-2}$.

The nanofiltration membranes that can be used according to the invention consist:
(i) of an organic porous material which plays the role of a support providing the mechanical strength of the membrane; said porous material is generally composed of cellulosic materials (for example, cellulose acetate), sulfonated materials, polyamide and polyimide materials, acrylic materials used alone or in the form of copolymers or of polymer alloys, fluorinated materials, or else polycarbonate and poly-propylene; and
(ii) of an active layer composed of at least 50% of polyamide, which covers said organic porous material; the active layer is preferably composed of at least 70%, and more preferentially of at least 90%, of polyamide.

The term "active layer" is intended to mean the surface of the nanofiltration membrane that is in contact with the sample to which the nanofiltration treatment is applied; in addition to the polyamide, said active layer may be composed, nonexhaustively, of poly-sulfones, polyethersulfones, polyimides and/or polyvinyl alcohol.

The term "polyamide" is intended to mean a polymer resulting from the polycondensation of carboxylic acid and amine functions; it is a question more particularly of aliphatic polyamides and aromatic polyamides.

The development of the nanofiltration step required several tests on various pilot apparatuses. The membrane selection results are detailed in example 1.

By virtue of this membrane selection, the phenolic fraction of the permeates obtained after nanofiltration is significantly enriched with low-molecular-weight phenolic compounds; by way of indication, hydroxytyrosol and tyrosol represent therein between 63 and 84% of the total phenolic compounds.

Preferably, the implementation of the nanofiltration step (c) is carried out under conditions such that the permeate flow is greater than or equal to 10 $kg \cdot h^{-1} \cdot m^{-2}$ (see example 2 hereinafter).

Step (d) of passing over the adsorbent polymeric matrix makes it possible to remove the nonphenolic compounds present in the permeate, in particular the minerals, the salts and the organic acids. The total phenolic compounds represent approximately 30% of the dry matter of the permeate; after passing over resin, they represent more than 80% of the dry matter of the eluate.

The polymeric matrix used in step (d) is preferably a styrene, acrylic or phenolic adsorbent resin; preferably, it is a polystyrene adsorbent resin.

The organic polar solvents or the aqueous solution of organic polar solvents that are of use for eluting the phenolic compounds adsorbed onto said matrix are in particular solvents that are acceptable in the food sector; preferably, they are a $C_1$-$C_4$ alcohol or a mixture of alcohols; preferentially, they are ethanol.

According to preferred embodiment variants of the present invention, the method also comprises one or more of the following steps:
  a step (a0), prior to step (a), of acidifying the wastewaters so as to reach a pH of less than or equal to 4.5.

The acidification of the wastewaters can be carried out with any acid that is compatible with human or animal food consumption. In particular, the acidification can be carried out with any organic acid, such as citric acid, tartaric acid, malic acid or lactic acid. Advantageously, the acidification is carried out with citric acid. Regardless of the acid used for carrying out step (a0) of the method according to the invention, those skilled in the art will be able to adjust the necessary amount of acid to be introduced into the wastewaters, for example by means of an iterative method consisting in adding small amounts of acid and then measuring the pH;
  a step (e) of concentrating, by distillation under vacuum, the eluate obtained in step (d).

According to one particular embodiment variant of the method, it comprises successively the steps (a0), (a), (b), (c), (d) and (e).

The method may also comprise three additional steps that are of use with a view to storage of the wastewaters before the implementation of the method according to the invention. These three steps, which are inserted between steps (a) and (b), are the following:
  (a1) concentration of the acidified and clarified vegetable waters for the storage thereof;
  (a2) storage of the concentrated acidified vegetable waters; then
  (a3) dilution of the concentrated acidified vegetable waters in a solvent at approximately 4% of dry matter before carrying out step (b).

Step (a1) can be carried out by means of a vacuum concentration technique.

The storage according to step (a2) is preferentially carried out at a temperature of between 6 and 15° C.

The solvent of step (a3) is preferably water.

The implementation of the method according to the invention results in a composition enriched with low-molecular-weight phenolic compounds which is also a subject of the present invention. This composition—hereinafter called composition A—advantageously comprises at least 40% of dry matter; this dry matter percentage is the ratio between the weight of the dry matter obtained after drying of the composition A and the total weight of the composition A; said dry matter is composed of at least 80% of total phenolic compounds; in particular, it comprises at least 30% of hydroxytyrosol and at least 10% of tyrosol.

This method has in particular the advantage of reproducibly producing a composition of phenolic compounds comprising minimal contents of hydroxytyrosol, of tyrosol and of other low-molecular-weight phenolic compounds, such as hydroxycinnamic acids, for instance ferulic acid, coumaric acid or cafeic acid, or esters thereof, for instance chlorogenic acid. This is an important criterion for subsequent use in the cosmetics or food industries, for example.

The composition A thus obtained is advantageously dried, for example by spray drying. Preferably, and in order to avoid the use of drying supports such as polysaccharide fillers, for instance dextrins or gums, a grape extract comprising at least 60% by weight of total polyphenols is used as drying support. Thus, the invention also relates to the use of a grape extract comprising at least 60% by weight of total polyphenols as a support for drying a composition A by spray drying.

The invention also relates to a method for preparing a powder titrated with respect to olive and grape phenolic and polyphenolic compounds, comprising the following steps:
  (e1) mixing a composition A with a grape extract comprising at least 60% of total polyphenols; said mixture comprises an amount of said composition A such that the dry matter of said composition A represents between 5 and 40% of the total dry matter of the mixture;
  (e2) drying the mixture obtained in step (e1), by spray drying.

The percentage of dry matter in the mixture of the composition A and the grape extract is the ratio between the weight of the dry matter measured after drying of said mixture and the total weight of said mixture.

Said grape extract preferably comprises at least 60% of total polyphenols, and more preferentially at least 90% of total polyphenols. The total polyphenol content of a grape extract may in particular be measured by the Folin-Ciocalteu method (Folin Singleton V L, Orthofer R, Lamuela-Raventos R M. Analysis of total phenols and other oxidation substrates and antioxidants by means of Folin-Ciocalteu reagent. Meth Enzymol 1999; 299: 152-178).

The grape extract can be obtained by passing grape marc piquette or aqueous extracts of grape seeds over an adsorbent resin, in particular a styrene, acrylic or phenolic adsorbent resin. Grape marc piquette is a solution obtained after steeping grape marc in water; grape marc is the solid part recovered at the end of the grape pressing step, it consists of all the skins and grape seeds and also the stalk.

According to one embodiment variant of this method, these two steps (e1) and (e2) follow step (e) of the method for extracting low-molecular-weight phenolic compounds according to the invention.

Drying by spray drying (or pulverization) is a technique for removing water by carrying it along, which consists in pulverizing a liquid product in a stream of hot air. In practical terms, this technique consists in injecting the liquid product to be dehydrated in the form of a fine fog at the top of a tower at the same time as a stream of very hot air runs through said tower; under the effect of the heat, the water evaporates and the dehydrated powder falls to the bottom of the tower.

Said method for preparing a powder titrated with respect to olive and grape phenolic and polyphenolic compounds produces a powder comprising at least 95% of phenolic and polyphenolic compounds.

The present invention also relates to a powder titrated with respect to olive and grape phenolic and polyphenolic compounds, comprising at least 95% of phenolic compounds, of which 5 to 40% of the dry matter comes from the composition A; the dry matter which comes from said composition A being composed of at least 80% of total phenolic compounds, including at least 30% of hydroxytyrosol and at least 10% of tyrosol, said composition.

Example 5 shows that the powders according to the invention exhibit a very good free-radical-scavenging activity. Specifically, this free-radical-scavenging activity is greater than the sum of the free-radical-scavenging activity of the composition A and of that of grape extracts taken separately, demonstrating a synergistic effect of the combination of the composition A and the grape extract polyphenols in the powders of the invention.

By way of indication, the powders titrated with respect to olive and grape phenolic and polyphenolic compounds obtained from olives and from grapeseed extracts have the following content ranges:

| Total phenolic compounds | from 60 to 100% |
|---|---|
| Procyanidins | from 18 to 50% |
| Hydroxytyrosol | from 1.5 to 16% |
| Tyrosol | from 0.5 to 8%. |

When the grape polyphenols come from grape marc, the powder comprises the following content ranges:

| Total phenolic compounds | from 60 to 100% |
|---|---|
| Procyanidins | from 9 to 25% |
| Anthocyans | from 1.2 to 8% |
| Hydroxytyrosol | from 1.5 to 16% |
| Tyrosol | from 0.5 to 8% |

The powders obtained according to this method are also subjects of the present invention.

The compositions A enriched with low-molecular-weight phenolic compounds and the powders according to the invention have many applications. They are of particularly marked interest in the cosmetics field, for their use as an agent for preventing oxidative stress in the skin (dermis and epidermis), as a free-radical scavenger, as an anti-aging agent; but also in the food sector, in particular for use as food supplements or else as a preservative.

The compositions A enriched with low-molecular-weight phenolic compounds and the powders according to the invention are particularly active as skin depigmenting and/or whitening agents; they thus promote elimination of pigmentary irregularities and spots on the skin.

The invention is now described in greater detail with regard to the examples which follow. It should be understood, however, that these examples are given only by way of illustration of the subject of the invention, of which they in no way constitute a limitation.

Example 1

Selection of a Nanofiltration Membrane

In order to optimize the separation of the low-molecular-weight phenolic compounds by nanofiltration, several commercial membranes were evaluated in terms of performance (permeate flow density) and retention.

The tests were carried out at 30±2° C. on a laboratory pilot apparatus (nominal volume of 3 l) in the planar configuration with a useful membrane surface area of about $1.5 \times 10^{-2}$ m$^2$. The selected transmembrane pressures range between 1 and 3 MPa and the tangential speed is in the region of 1 m·s$^{-1}$.

In order to evaluate the feasibility of the separation of low-molecular-weight phenolic compounds, nine nanofiltration membranes were preselected (supplier Microdyn Nadir, Dow Filmtec, GE Osmonics, Toray, Koch). These membranes have a cutoff threshold of between 150 and 400 Da (values stated by the manufacturers).

They were tested on a standard vegetable water containing 4% of dry matter without concentration, i.e. with a volume reduction factor close to 1. Depending on the membrane and the transmembrane pressure used, the permeate flow densities vary between 3 and 133 kg·h$^{-1}$·m$^{-2}$.

The results obtained are given in table I hereinafter.

TABLE I

Nanofiltration results obtained on the various membranes tested

| Membranes | | | Permeate | Retention (%) | | |
|---|---|---|---|---|---|---|
| Supplier | Nature of active layer polymer | Reference | flow density (L · h$^{-1}$ · m$^{-2}$) | Dry matter | Total polyphenols | Hydroxy-tyrosol |
| Mycrodin Nadir | Polyethersulfones | NP030 | 3-5 | 78 | 51 | 17 |
| | | NP010 | 13-23 | 52-73 | 41-46 | 9 |
| Dow Filmtec | Polyamides | NF270 | 20-56 | 90-96 | 58-59 | 26-43 |
| | | NF200 | 14-42 | 87-94 | 56-64 | 22-40 |
| | | NF90 | 3-19 | >99 | 98 | 99 |
| GE Osmonics | Polyamides | DK | 20-92 | 92-99 | 78-82 | 1-40 |
| | | DL | 27-133 | 75-97 | 51-78 | 1-44 |
| Toray | Polyvinyl alcohol/polyamides | UTC60 | 14-45 | 90-94 | 56-66 | 22-39 |
| Koch | Polyamides | MPF34 | 7-17 | >99 | 93 | 87 |

The membranes tested retain between 52 and 99% of the dry matter and between 41 and 98% of total polyphenols of the vegetable waters tested (determined with the Folin-Ciocalteu method, Folin Singleton V L, Orthofer R, Lamuela-Raventos R M. *Analysis of total phenols and other oxidation substrates and antioxidants by means of Folin-Ciocalteu reagent*. Meth Enzymol 1999; 299: 152-178).

The retention of hydroxytyrosol, the main low-molecular-weight phenolic compound, is lower; the membranes tested retain between 1 and 44% of the hydroxytyrosol present in the vegetable waters treated, with the exception of the Dow Filmtec NF90 and Koch MPF34 membranes.

Although the membranes are a priori similar, it is observed that the overall performance levels of the method (permeate flow density) and the separation performance levels (retention) are closely linked to the choice of the nanofiltration membrane.

In the context of the application envisioned, the most suitable membranes are those which make it possible to simultaneously obtain a low retention of hydroxytyrosol, a high retention of dry matter and of total polyphenols and, finally, a high permeate flow density. Among the membranes tested, most of the membranes of which the active layer is composed of polyamides produce advantageous results. Those of which the active layer consists of polyethersulfones only partially meet these criteria.

Example 2

Influence of the Concentration of the Vegetable Waters on the Efficiency of the Nanofiltration Step In order to evaluate the impact of the concentration of the vegetable waters on the permeate flow density and the retention, vegetable waters having a dry matter content ranging from 3.5 to 22% were treated. For these tests, two membranes among those with the highest performance levels that were tested in example 1 are selected: GE Osmonics Desal DL and DK.

As in example 1, the tests were carried out at 30° C. on a laboratory pilot apparatus in the planar configuration with a useful membrane surface area of about $1.5 \times 10^{-2}$ m². The transmembrane pressures used range between 20 bar (2 MPa) and 30 bar (3 MPa), and the tangential speed is in the region of 1 m·s$^{-1}$.

The results obtained are given in table II.

TABLE II

| Membrane | Vegetable water dry matter (%) | Transmembrane pressure (bar) | Permeate flow (kg · h$^{-1}$ · m$^{-2}$) |
|---|---|---|---|
| GE Osmonics Desal DL | 4 | 20 | 95.4 |
| | | 25 | 105.3 |
| | | 30 | 132.7 |
| | 13 | 20 | 10.4 |
| | | 25 | 19.5 |
| | | 30 | 29.8 |
| | 22 | 20 | <0.8 |
| | | 25 | 1.1 |
| | | 30 | 3.2 |
| GE Osmonics Desal DK | 4 | 20 | 63.2 |
| | | 25 | 78.2 |
| | | 30 | 91.9 |
| | 13 | 20 | 5.0 |
| | | 25 | 12.7 |
| | | 30 | 22.5 |
| | 22 | 20 | <0.8 |
| | | 25 | <0.8 |
| | | 30 | 0.8 |

For both membranes, the permeate flow decreases rapidly with the increase in dry matter content. For example, at 20 bar, the permeate flow density is divided by 10 when the dry matter content goes from 4 to 13%. At 22% of dry matter, the permeate flow densities are very low: the pressure must be maintained above 25 bar in order to obtain permeate flow densities of a few kg·h$^{-1}$·m$^{-2}$.

These results show that, in order to guarantee a flow of greater than 10 kg·h$^{-1}$·m$^{-2}$ under the operating conditions tested, it is difficult to exceed 13 to 15% of dry matter. This content corresponds to a volume reduction factor of between 3 and 4, i.e. a permeate production yield of around 70%.

The volume reduction factor (VRF) is defined as the ratio between the initial product volume and the final retentate volume, i.e. VRF=$V_0/V_r$; as $V_0=V_r+V_p$, VRF is directly linked to the permeate production volume yield X=$V_p$/V0, i.e. as a percentage X=100×(1−1/VRF).

It is noted, moreover, that the retentions are barely affected by the dry matter content of the vegetable waters of the feed; the amounts of dry matter and of total polyphenols in the retentate decrease slightly when the concentration of the vegetable waters increases.

Example 3

Semi-Industrial Scale Nanofiltration Tests

The laboratory tests made it possible to evaluate the technical feasibility of the nanofiltration method for enriching the product with low-molecular-weight phenolic compounds. They also made it possible to select commercial membranes suitable for carrying out the operation. In order to evaluate the method on a scale more suitable for industrial use, tests were carried out using spiral nanofiltration modules having a useful surface area of 2.5 m². The apparatus used has a nominal capacity of 80 l. The transmembrane pressure selected is between 2 and 3 MPa, the temperature is 30° C. and the circulation flow rate is $1.7 \times 10^{-4}$ m³·s$^{-1}$.

The first test is carried out on the same membranes as those presented in example 2, i.e. the GE Osmonics Desal DL and DK membranes. During this test, the permeate is extracted continually until a volume reduction factor of 8 is reached.

The results obtained in terms of performance are consistent with those obtained on a laboratory pilot: the permeate flow density decreases when the percentage of dry matter of the vegetable waters increases. The maximum volume reduction factor in order to obtain a permeate flow density of greater than 10 kg·h$^{-1}$·m$^{-2}$ is between 4.5 and 6, i.e. a permeate production yield of around 80%. For volume reduction factors of between 2 and 6, the dry matter of the permeate is enriched 2- to 4-fold with total phenolic compounds and 5- to 13-fold with hydroxytyrosol.

Additional tests were carried out with the same two spiral membrane modules of 2.5 m² and under conditions similar to those described above. These tests are aimed at verifying the stability of the performance levels of the operation by simulating continuous operation with two successive concentration stages. The first stage corresponds to a volume reduction factor of 2 (i.e. a permeate production yield of 50%) and the second corresponds to a volume reduction factor of 8 (i.e. a production yield of 75%).

The permeate flow densities are approximately 15 times lower in the second stage compared with the first. The flow densities, verified over hold durations of 120 minutes, are stable over time in both stages. In terms of retention, the results corroborate those previously obtained. Continuous industrial implementation of the method can therefore be readily envisioned.

Example 4

Implementation of the Method According to the Invention on an Industrial Scale

In order to validate the method overall, a test was carried out on the industrial scale, with all the steps of the method according to the invention being integrated.

For this test, 19.3 m³ of fresh vegetable waters acidified with citric acid at pH 4.2 were used.

These vegetable waters are first of all clarified by filtration through a rotary filter under vacuum and then treated by means of ultrafiltration on an apparatus equipped with 37.2 m² of tubular ceramic membranes having a cutoff threshold of 150 kDa. The permeate obtained (13.9 m³) is then nanofiltered on an apparatus equipped with 18 m² of GE Osmonics Desal DL spiral organic membranes. The nanofiltration permeate (10.6 m³) is then treated on Relite SP411® absorbent resins. After elution with 80% ethanol and concentration of the alcoholic eluate under vacuum, 45.7 kg of composition enriched with low-molecular-weight phenolic compounds containing 48% of dry matter are obtained. This composition contains 41.7% of polyphenols ($A_{280\ nm}$ eq. catechin, i.e. expressed in catechin equivalent and measured with a spectrophotometer at 280 nm according to J. Zhishen, T. Mengcheng, W. Jianming (1999) The determination of flavonoid contents in mulberry and their scavenging effects on superoxide radicals, *J Food Chem*, Volume 64, pp 555-559), 17% of hydroxytyrosol and 6% of tyrosol (measured by high performance liquid chromatography, HPLC).

The composition enriched with low-molecular-weight phenolic compounds is finally dried by spray drying, with a grape extract. Prior to the drying, the composition and the grape extract are mixed such that the dry matter of the mixture is composed of 80% of grape dry matter and 20% of dry matter of said composition. The final product obtained is a fluid powder which does not set to a solid. It contains only polyphenols (100%, $A_{280\ nm}$ eq. catechin). It is made up of 17.4% of procyanidins, 7.6% of hydroxytyrosol, 2.7% of tyrosol (HPLC) and 3.1% of anthocyans (measured according to the method of Riberau-Gayon et al., 1975, Sciences et techniques du vin [Wine sciences and techniques], volume III, Dunod, Paris).

The drying of said composition under the same conditions but with a grapeseed polyphenol support (in the same way, the mixture is such that the dry matter of the mixture is composed of 80% of grapeseed dry matter and 20% of dry matter of the composition) also results in a fluid powder, which does not set to a solid and which is made up only of polyphenols. This second powder is made up of 31.2% of procyanidins (vanillin method, Broadhurst R. B., Jones W. T. 1978. Analysis of condensed tannins using acidified vanillin. J. Science Food Agriculture, 29:788-794), 6.9% of hydroxytyrosol and 2.5% of tyrosol (HPLC).

Example 5

Measurement of the Free-Radical-Scavenging Activity of the Compositions and Powders According to the Invention The free-radical-scavenging properties of the compositions enriched with low-molecular-weight phenolic compounds, obtained from wastewaters, and of the powders obtained by drying said compositions with grape polyphenols as a drying support, were evaluated by the ORAC method.

The ORAC, for oxygen radical absorbance capacity, method (CAO et al. 1993, Free Radical Biol. Med. 14, 303-311; PRIOR et al. 2003, J. Agric. Food Chem. 51, 3273-3279) is a method for measuring free-radical-scavenging activity in vitro. The principle of said method is based on the use of fluorescein, a natural fluorescent molecule which is very sensitive to free radicals. The free radicals, which are produced by AAPH (2,2'-azobis(2-amidinopropane) dihydrochloride), in the reaction medium react with the antioxidants of the composition or the powder to be tested. As soon as all the free radicals have reacted with the antioxidants of the composition or the powder to be tested, they destroy the fluorescein and the fluorescence disappears. The ORAC value is determined by measuring the area under the curve of the fluorescence as a function of time. The results are compared with the data obtained with Trolox (vitamin E analog); they are expressed in micromoles of Trolox equivalents (TEQ) per g, or kg or per liter.

The ORAC values measured in the context of these tests appear in table III.

TABLE III

| Composition | ORAC value of the composition | ORAC value of the dry matter |
|---|---|---|
| composition enriched with low-molecular-weight phenolic compounds of wastewaters | 6340 micromol TEQ/g | 13200 micromol TEQ/g |
| Polyphenols of a grapeseed extract | — | 19000 micromol TEQ/g |
| Polyphenols of a grape extract | — | 13100 micromol TEQ/g |
| powder obtained with the grapeseed extract as drying support | 19300 micromol TEQ/g | — |
| powder obtained with the grape extract as drying support | 15100 micromol TEQ/g | — |

For a composition enriched with low-molecular-weight phenolic compounds from wastewaters, the ORAC value is 6340 micromol TEQ/g; given that the dry matter of this extract is 48%, this corresponds to 13200 micromol TEQ/g of dry matter.

The ORAC value of the grapeseed extract and that of the grape extract are, respectively, 19 000 micromol TEQ/g and 13 100 micromol TEQ/g.

Thus, for the powder containing 80% of dry matter of grapeseed extract and 20% of dry matter of olive extract, a theoretical ORAC value calculated from the ORAC values of the corresponding dry matters of 17 840 micromol TEQ/g should be expected; however, the measurement of the ORAC value is 19 300 micromol TEQ/g.

Similarly, for the mixture containing 80% of dry matter of grape extract and 20% of dry matter of olive extract, an ORAC value of 13 120 micromol TEQ/g should be expected, and the measured value is 15 100 micromol TEQ/g.

The ORAC values obtained on the powders according to the invention are therefore 8 to 15% higher than those expected, which shows a synergistic effect, in terms of the free-radical-scavenging activity, of the combination of olive low-molecular-weight phenolic compounds and grape polyphenols.

Example 6

Comparative Example of Implementation of the Method According to the Invention on an Industrial Scale with a Nanofiltration Membrane not Having the Required Characteristics Another test of implementation of the method on an industrial scale is carried out with a Koch SR3N2 membrane.

For this test, 28 m³ of vegetable waters are acidified with citric acid so as to reach a pH of 4.2.

The acidified vegetable waters are then ultrafiltered on an apparatus equipped with 37.2 m² of tubular ceramic membranes having a cutoff threshold of 150 kDa.

The permeate obtained (24 m³) is nanofiltered on an apparatus equipped with 18 m² of Koch SR3N2 spiral organic membranes. The nanofiltration permeate (18 m³) is treated on a Relite SP411 adsorbent resin. After dilution with 80% ethanol and concentration of the alcoholic eluate under vacuum, 41 kg of composition enriched with low-molecular-weight phenolic compounds containing 48.8% of dry matter are obtained. This composition contains 37.6% of polyphenols ($A_{280\ nm}$ eq. catechin), 11% of hydroxytyrosol and 4% of tyrosol (HPLC). In this composition, the hydroxytyrosol/total phenols ratio is only 29.3 g/100 g. This test confirms the results of example 1; the selectivity of this nanofiltration membrane is insufficient to obtain a composition enriched with phenolic compounds of interest.

The invention claimed is:

1. A method for preparing a composition enriched with low-molecular-weight phenolic compounds from olive wastewaters, the method consisting of:
    (a) acidification of olive wastewaters so as to reach a pH of less than or equal to 4.3 a step of clarification of said acidified olive wastewaters;
    concentration of the acidified and clarified olive wastewaters by vacuum concentration for storage thereof; storage of the concentrated acidified olive wastewaters; and then dilution of the concentrated acidified olive wastewaters in a solvent at approximately 4% of the acidified, clarified, and concentrated olive wastewaters;
    (b) a step of tangential ultrafiltration of the diluted wastewaters obtained in step (a) through a tubular ceramic membrane having a cutoff threshold of between 100 and 200 kDa to obtain a permeate, and of recovery of the permeate;
    (c) a step of nanofiltration of said permeate obtained in step (b) through a spiral organic membrane having a cutoff threshold of between 150 and 400 Da at a pressure of between 1 and 3 MPa to obtain a permeate; said membrane is such that it comprises an active layer comprising at least 50% of polyamide and that it makes it possible to obtain a retentate comprising at least 80% of dry matter contained in said wastewaters, and at most 25% of hydroxytyrosol,
    (d) a step of adsorption of the phenolic compounds contained in the permeate obtained in step (c) by passing the latter over a polymeric matrix, followed by elution of the phenolic compounds adsorbed on said matrix, with an organic polar solvent, and obtaining of an eluate;
    (e) a step of concentration, by distillation under vacuum, of the eluate obtained in step (d) and obtaining a Composition A; and
    (f) a step of drying said Composition A.

2. The method according to claim 1, wherein said step of drying consists of the following steps:
    (f1) mixing said Composition A with a grape extract to obtain a mixture comprising at least 60% of total polyphenols; said mixture comprises an amount of said Composition A such that the dry matter of said Composition A represents between 5 and 40% of the total dry matter of the mixture;
    (f2) drying the mixture obtained in step (e1), by spray drying to obtain a powder.

3. The method according to claim 1, wherein said steps (a), (b), (c), (d), and (e) are carried out successively.

4. A method for preparing a composition enriched with low-molecular-weight phenolic compounds from olive wastewaters, the method consisting of:
    (a) a step of clarification of said wastewaters;
    (b) a step of tangential ultrafiltration of the clarified wastewaters obtained in step (a) through a tubular ceramic membrane having a cutoff threshold of between 100 and 200 kDa to obtain a permeate, and of recovery of the permeate;
    (c) a step of nanofiltration of said permeate obtained in step (b) through a spiral organic membrane having a cutoff threshold of between 150 and 400 Da at a pressure of between 1 and 3 MPa to obtain a permeate; said membrane is such that it comprises an active layer comprising at least 50% of polyamide and that it makes it possible to obtain a retentate comprising at least 80% of dry matter contained in said wastewaters, and at most 25% of hydroxytyrosol,
    (d) a step of adsorption of phenolic compounds contained in the permeate obtained in step (c) by passing said permeate over a polymeric matrix, followed by elution of the phenolic compounds adsorbed on said matrix, with an organic polar solvent, and obtaining of an eluate;
    (e) a step of concentration, by distillation under vacuum, of the eluate obtained in step (d) and obtaining a Composition A; and
    a step of drying said Composition A.

5. A method of making a food product comprising the step of adding a powder obtained by the method according to claim 2 to a food product.

* * * * *